United States Patent

Li et al.

[11] Patent Number: 6,020,332
[45] Date of Patent: Feb. 1, 2000

[54] FLUORINE-CONTAINING DIPHENYL ACRYLAMIDE ANTIMICROBIAL AGENTS

[75] Inventors: Zongcheng Li; Changling Liu; Wucheng Liu, all of Liaoning, China

[73] Assignee: Shenyang Research Institute of Chemical Industry, China

[21] Appl. No.: 09/020,333

[22] Filed: Feb. 9, 1998

Related U.S. Application Data

[60] Provisional application No. 60/038,700, Feb. 20, 1997.

[51] Int. Cl.⁷ .......................... A01N 43/84; C07D 265/30
[52] U.S. Cl. ...................... 514/237.5; 544/170; 544/175; 544/176
[58] Field of Search .................. 514/141, 237.5; 544/176, 170, 175

[56] References Cited

U.S. PATENT DOCUMENTS

| | | |
|---|---|---|
| 4,753,934 | 6/1988 | Nickl et al. . |
| 4,910,200 | 3/1990 | Curtze et al. . |
| 5,424,480 | 6/1995 | Vermehren et al. . |

FOREIGN PATENT DOCUMENTS

| | | |
|---|---|---|
| 0208999 | 1/1987 | European Pat. Off. . |
| 0219756 | 4/1987 | European Pat. Off. . |
| 0520585 | 12/1992 | European Pat. Off. . |
| 0601477 | 6/1994 | European Pat. Off. . |
| 3615448 | 11/1987 | Germany . |

*Primary Examiner*—Shailendra Kumar
*Attorney, Agent, or Firm*—Banner & Witcoff, Ltd.

[57] ABSTRACT

Fluorine-containing diphenyl acrylamide of general formula (I) have antimicrobial properties.

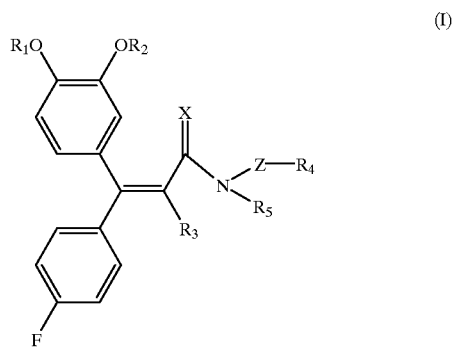

wherein $R_1$ and $R_2$ are independently selected from $(C_1-C_6)$ alkyl group, alkyl group, $(C_1-C_6)$alkoxy group, halo$(C_1-C_6)$ alkyl group, halo$(C_1-C_6)$alkoxy group, $(C_1-C_6)$alkoxy $(C_1-C_6)$alkyl group, $(C_3-C_6)$cycloalkyl group, $(C_3-C_6)$ cycloalkyl$(C_1-C_4)$alkyl group, $(C_2-C_6)$alkenyl group, halo $(C_2-C_6)$alkenyl group, $(C_3-C_6)$alkynyl group, halo$(C_3-C_6)$ alkynyl group, aryl group, aryloxy$(C_1-C_{12})$alkyl group, aralkyl group, heterocyclic group;

or $R_1$ and $R_2$ when taken together may form a 5 or 6-membered ring such that;

when $R_1$ and $R_2$ are in a 5 membered ring $R_1$ and $R_2$ taken together is $C(R_6R_7)$; and when $R_1$ and $R_2$ are in a 6 membered ring $R_1$ and $R_2$ taken together is $CHR_6-CHR_7$;

where $R_6$ and $R_7$ are independently selected from hydrogen, $(C_1-C_6)$alkyl group or halogen.

7 Claims, No Drawings

FLUORINE-CONTAINING DIPHENYL ACRYLAMIDE ANTIMICROBIAL AGENTS

This application is a continuation of provisional application Ser. No. 60/038,700, Feb. 20, 1997.

BACKGROUND OF THE INVENTION

U.S. Pat. No. 4,753,934 describes antimicrobial diphenyl acrylamide compounds that can be used as antimicrobial agents in agriculture. However, the protective effect of these compounds against plant pests is poor, and more active compounds are needed. For example, for protection against cucumber downy mildew, antimicrobial agents such as metalaxyl, aluminium phosphide, chlorothalonil, and probamocarb do not have satisfactory effect. In order to meet requirements in agriculture and horticulture, the present invention intends to propose a new fluorine-containing diphenyl acrylamide antimicrobial agents and its composition.

SUMMARY OF THE INVENTION

The fluorine-containing diphenyl acrylamide antimicrobial compounds of the present invention have the general formula (I)

(I)

[Structural formula showing a diphenyl acrylamide with $R_1O$ and $OR_2$ substituents on one phenyl ring, F on another phenyl ring, and an amide group with X, $R_3$, $R_4$, $R_5$, Z substituents]

wherein $R_1$ and $R_2$ are independently selected from $(C_1-C_6)$alkyl, $(C_1-C_6)$alkoxy group, halo$(C_1-C_6)$alkyl group, halo$(C_1-C_6)$alkoxy group, $(C_1-C_6)$alkoxy$(C_1-C_6)$alkyl group, $(C_3-C_6)$cycloalkyl group, $(C_3-C_6)$cycloalkyl$(C_1-C_4)$alkyl group, $(C_2-C_6)$alkenyl group, halo$(C_2-C_6)$alkenyl group, $(C_3-C_6)$alkynyl group, halo$(C_3-C_6)$alkynyl group, aryl group, aryloxy$(C_1-C_{12})$alkyl group, aralkyl group, heterocyclic group;

or $R_1$ and $R_2$ when taken together may form a 5 or 6-membered ring such that;
 when $R_1$ and $R_2$ are in a 5 membered ring $R_1$ and $R_2$ taken together is $C(R_6R_7)$; and
 when $R_1$ and $R_2$ are in a 6 membered ring $R_1$ and $R_2$ taken together is $CHR_6$–$CHR_7$:
where $R_6$ and $R_7$ are independently selected from hydrogen, $(C_1-C_6)$alkyl group or halogen $R_3$ is hydrogen, halo, $(C_1-C_6)$alkyl group, $(C_1-C_6)$alkoxy group, cyano group, nitro group, triazole group, pyrazole group, imidazole group;

X is oxygen, sulfur or NH;

Z is a bond or an oxygen;

$R_4$ and $R_5$ are independently selected from hydrogen, $(C_1-C_6)$alkyl group, $(C_1-C_6)$alkoxy group, $(C_1-C_6)$ alkoxy$(C_1-C_6)$alkyl group, $(C_1-C_6)$alkoxy$(C_2-C_6)$ alkenyl group, halo$(C_1-C_6)$alkyl group, halo$(C_1-C_6)$ alkoxy group, halo$(C_1-C_6)$alkoxy$(C_3-C_6)$alkynyl group, $(C_1-C_6)$alkoxycarbonyl, di$(C_1-C_6)$ alkylaminocarbonyl group, $(C_3-C_6)$cycloalkyl group, $(C_3-C_6)$cycloalkyl$(C_1-C_4)$alkyl group, aralkyl group, arylcarbonyl group, heterocyclic carbonyl group, heterocyclic$(C_1-C_6)$alkyl group;

or when taken together may form a 5-membered ring such as a triazole group, pyrazole group, imidazole group, tetrahydropyrrole group, isoxazole group or a 6-membered ring such as a morpholine group, piperidine, piperazine, pyrazine, or pyrimidine.

The language Z is a bond is understood to mean that the Z substituent is not present and the nitrogen atom is bonded directly to $R_4$.

The aforementioned $(C_1-C_6)$alkyl group, $(C_1-C_6)$alkoxy group, $(C_2-C_6)$alkenyl group, $(C_3-C_6)$alkynyl and $(C_3-C_6)$ cycloalkyl groups may be optionally substituted with up to three substituents selected from the group consisting of nitro, trihalomethyl and cyano.

The term alkyl group includes both branched and straight chained alkyl groups from 1 to 6 carbon atoms. Typical alkyl groups are methyl, ethyl, n-propyl, iso-propyl, n-butyl, sec-butyl, isobutyl, t-butyl, n-pentyl, isopentyl, and n-hexyl and the like. The term haloalkyl refers to an alkyl group substituted with 1 to 3 halogens.

The term alkoxy group includes both branched and straight chained alkoxy groups from 1 to 6 carbon atoms. Typical alkoxy groups are methoxy, ethoxy, n-propoxy, iso-propoxy, n-butoxy, sec-butoxy, isobutoxy, t-butoxy, n-pentoxy, isopentoxy, and n-hexoxy and the like. The term haloalkoxy refers to an alkoxyl group substituted with 1 to 3 halogens.

The term alkenyl group refers to an ethylenically unsaturated hydrocarbon group, straight or branched, having a chain length of 2 to 6 carbon atoms and 1 or 2 ethylenic bonds. The term haloalkenyl group refers to an alkenyl group substituted with 1 to 3 halogen atoms. The term alkynyl group refers to an unsaturated hydrocarbon group, straight or branched, having a chain length of 3 to 6 carbon atoms and 1 or 2 acetylenic bonds.

The term di$(C_1-C_6)$alkylaminocarbonyl group refers to aminocarbonyl group to which the amino moiety has attached two $(C_1-C_6)$alkyl groups. Typical di$(C_1-C_6)$ alkylaminocarbonyl groups are dimethylaminocarbonyl, diethylaminocarbonyl, dipropylaminocarbonyl and ethylmethylaminocarbonyl.

The term cycloalkyl group refers to a saturated ring system having 3 to 7 carbon atoms.

The term aryl group includes phenyl or napthyl, which maybe substituted with up to three substituents selected from the group consisting of halogen, cyano, nitro, trihalomethyl, phenyl, phenoxy, $(C_1-C_4)$alkyl, $(C_1-C_4)$ alkylthio, $(C_1-C_4)$alkylsulfoxide, $(C_1-C_6)$alkoxy and halo $(C_1-C_4)$alkyl.

Typical aryl group substituents include but are not limited to 4-chlorophenyl, 4-fluorophenyl, 4-bromophenyl, 2-methoxyphenyl, 2-methylphenyl, 3-methylphenyl, 4-methylphenyl, 2,4-dibromophenyl, 3,5-difluorophenyl, 2,4,6-trichlorophenyl, 4-methoxyphenyl, 2-chloronapthyl, 2,4-dimethoxyphenyl, 4-(trifluoromethyl)phenyl and 2-iodo-4-methylphenyl.

The term arylcarbonyl group includes phenylcarbonyl, the phenyl portion which maybe substituted with up to three substituents selected from the group consisting of halogen, cyano, nitro, trihalomethyl, phenyl, phenoxy, ($C_1$–$C_4$)alkyl, ($C_1$–$C_6$)alkoxy and halo($C_1$–$C_4$)alkyl. Typical phenylcarbonyl groups include but are not limited to 4-chlorobenzoyl, 4-fluorobenzoyl, 4-bromobenzoyl, 2-methoxybenzoyl, 2-methylbenzoyl, 3-methylbenzoyl, 4-methylbenzoyl, 2,4-dibromobenzoyl, 3,5-difluorobenzoyl, 2,4,6-trichlorobenzoyl, 4-methoxybenzoyl, 2,4-dimethoxybenzoyl, 4-(trifluoromethyl)benzoyl and 2-iodo-4-methylbenzoyl.

The term heterocyclic group refers to a optionally substituted 5 or 6 membered unsaturated ring containing one, two or three heteroatoms, preferably one or two heteroatoms selected from oxygen, nitrogen and sulfur or is a bicyclic unsaturated ring system containing up to 10 atoms including one heteratom selected from oxygen, nitrogen and sulfur. Examples of heterocycles includes but is not limited to 2-, 3- or 4-pyridine, pyrazine, 2-, 4-, or 5-pyrimidine, pyridazinel, triazole, imidazole, 2- or 3-thiophene, 2- or 3-furan, pyrrole, oxazole, isoxazole, thiazole, isothiazole, oxadiazole, thiadiazole, quinoline and isoquinoline. The heterocyclic ring may be optionally substituted with upto two substituents independently selected from ($C_1$–$C_6$) alkyl, ($C_1$–$C_6$) alkoxy, hydroxy, halogen, cyano, ($C_1$–$C_6$) alkoxycarbonyl, nitro and trihalomethyl.

The term heterocyclic carbonyl group refers to a heterocyclic group bonded through a carbon of the heterocyclic ring to a carbonyl group. Typical examples of heterocyclic carbonyl groups are 2- or 3-furoyl, 2- or 3-nicotinoyl and 4-isonicotinoyl.

The term aralkyl is used to describe a group wherein the alkyl chain is from 1 to 10 carbon atoms and can be branched to straight chain, preferably a straight chain, with the aryl portion, as defined above, forming a terminal portion of the aralkyl moiety. Typical aralkyl moieties are optionally substituted benzyl, phenethyl, phenpropyl and phenbutyl moieties. Typical benzyl moieties are 2-chlorobenzyl, 3-chlorobenzyl, 4-chlorobenzyl, 2-fluorobenzyl, 3-fluorobenzyl, 4-fluorobenzyl, 4-trifluoromethylbenzyl, 2,4-dichlorobenzyl, 2,4-dibromobenzyl, 2-methylbenzyl, 3-methylbenzyl, and 4-methylbenzyl. Typical phenethyl moieties are 2-(2-chlorophenyl)ethyl, 2-(3-chlorophenyl)ethyl, 2-(4-chlorophenyl)ethyl, 2-(2-fluorophenyl)ethyl, 2-(3-fluorophenyl)ethyl, 2-(4-fluorophenyl)ethyl, 2-(2-methylphenyl)ethyl, 2-(3-methylphenyl)ethyl, 2-(4-methylphenyl)ethyl, 2-(4-trifluoromethylphenyl)ethyl, 2-(2-methoxyphenyl)ethyl, 2-(3-methoxyphenyl)ethyl, 2-(4-methoxyphenyl)ethyl, 2-(2,4-dichlorophenyl)ethyl, 2-(3,5-dimethoxyphenyl)ethyl. Typical phenpropyl moieties are 3-phenylpropyl, 3-(2-chlorophenyl)propyl, 3-(3-chlorophenyl)propyl, 3-(4-chlorophenyl)propyl, 3-(2,4-dichlorophenyl)propyl, 3-(2-fluorophenyl)propyl, 3-(3-fluorophenyl)propyl, 3-(4-fluorophenyl)propyl, 3-(2-methylphenyl)propyl, 3-(3-methylphenyl)propyl, 3-(4-methylphenyl)ethyl, 3-(2-methoxyphenyl)propyl, 3-(3-methoxyphenyl)propyl, 3-(4-methoxyphenyl)propyl, 3-(4-trifluoromethyl-phenyl)propyl, 3-(2,4-dichlorophenyl)propyl and 3-(3,5-dimethoxyphenyl)propyl. Typical phenbutyl moieties include are 4-phenylbutyl, 4-(2-chlorophenyl)butyl, 4-(3-chlorophenyl)butyl, 4-(4-chlorophenyl)butyl, 4-(2-fluorophenyl)butyl, 4-(3-fluorophenyl)butyl, 4-(4-fluorophenyl)butyl, 4-(2-methylphenyl)butyl, 4-(3-methylphenyl)butyl, 4-(4-methylphenyl)butyl, 4-(2,4-dichlorophenyl)butyl, 4-(2-methoxyphenyl)butyl, 4-(3-methoxyphenyl)butyl and 4-(4-methoxyphenyl)butyl.

Halogen or halo is defined as iodo, fluoro, bromo and chloro moieties.

Because of the C=C double bond the novel compounds of the general Formula I may be obtained in preparation as E/Z isomeric mixtures. These isomers can be separated into individual components by conventional means. Both the individual isomeric compounds and mixtures thereof form subjects of the invention and can be used as fungicides.

DETAILED DESCRIPTION OF THE INVENTION

A preferred embodiment of this invention is the compounds of Formula (I) where X is O, Z is a direct bond, $R_1$ and $R_2$ is ($C_1$–$C_6$)alkyl, $R_3$ is hydrogen or cyano and $R_4$ and $R_5$ are independently selected from ($C_1$–$C_6$)alkyl, ($C_1$–$C_6$) alkoxy or when taken together may form a 5-membered ring such as a triazole group, pyrazole group, imidazole group, tetrahydropyrrole group or a 6-membered ring such as a morpholine group.

A more preferred embodiment of this invention are the compounds Formula (I) where $R_1$ and $R_2$ are methyl, $R_3$ is hydrogen, $R_4$ and $R_5$ when taken together is a morpholine.

Among the compounds of this invention, those having high activity are:

Compound 1: 3-(4-Fluorophenyl)-3-(3, 4-dimethoxyphenyl)acryloyl) morpholine

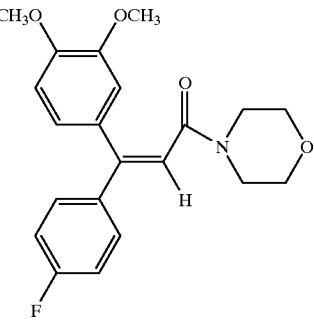

Compound 2: 3-(4-Fluorophenyl)-3-(3-methoxy-4-ethoxyphenyl)acryl morpholine

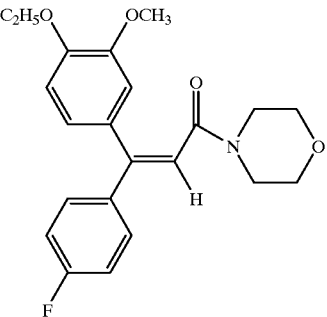

-continued

Compound 3: 3-(4-Fluorophenyl)-3-(3-ethoxy-4-methoxyphenyl) acryl morpholine

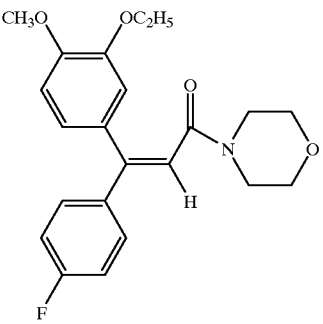

Compound 4: 3-(4-Fluorophenyl)-3-(3, 4-dimethoxyphenyl)-N-methoxy-N-methyl-acrylamide

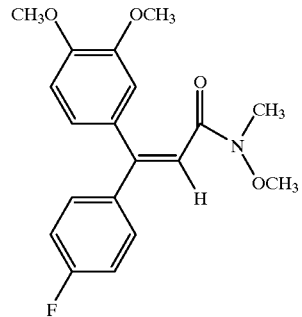

Compound 5: 3-(4-Fluorophenyl)-3-(3-ethoxy-4-methoxyphenyl)-N-methoxy-N-methyl acrylamide

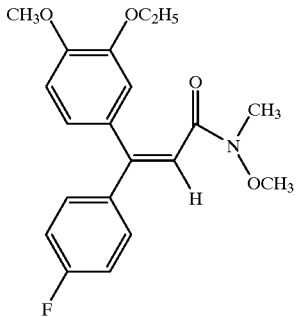

Compound 6: 3-(4-Fluorophenyl)-3-(3-methoxy-4-ethoxyphenyl)-N-methoxy-N-methyl acrylamide

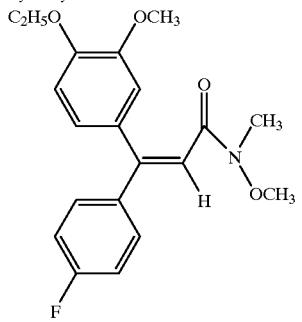

The title compounds of this invention can be prepared by the following methods described in Methods 1 to 4.

Method 1: In method 1 a substituted benzophenone is reacted with a diethylphosphonoacetamide as described in *Chem. Pharm. Bull.* 1394–1402, 1980 and U.S. Pat. No. 4,753,934. The preparation of the substituted benzophenones (II) are described in *J. Med. Chem.* 1140, 1979 and in U.S. Pat. Nos. 4,912,000 and 4,753,934.

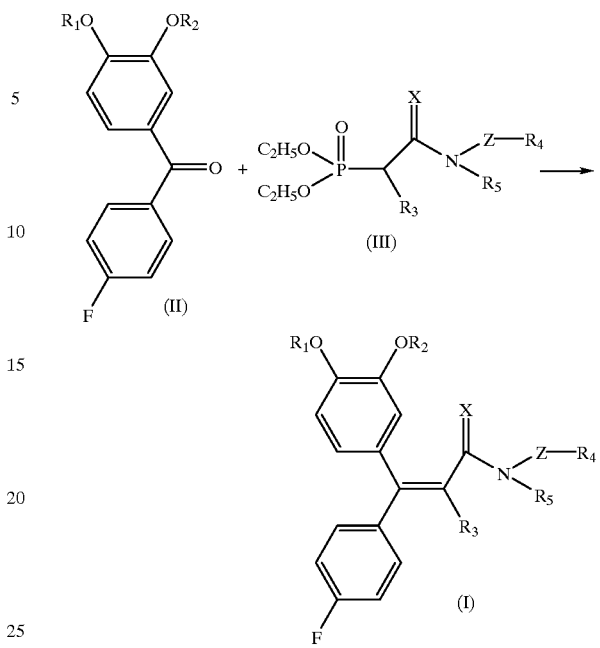

Method 2: In method 2 a substituted benzophenone is reacted with an disubstituted amide or thioamide (IV) and for $R_3$=hydrogen is described in U.S. Pat. No. 4,912,217 and for $R_3$=cyano is described in U.S. Pat. No. 4,753,934.

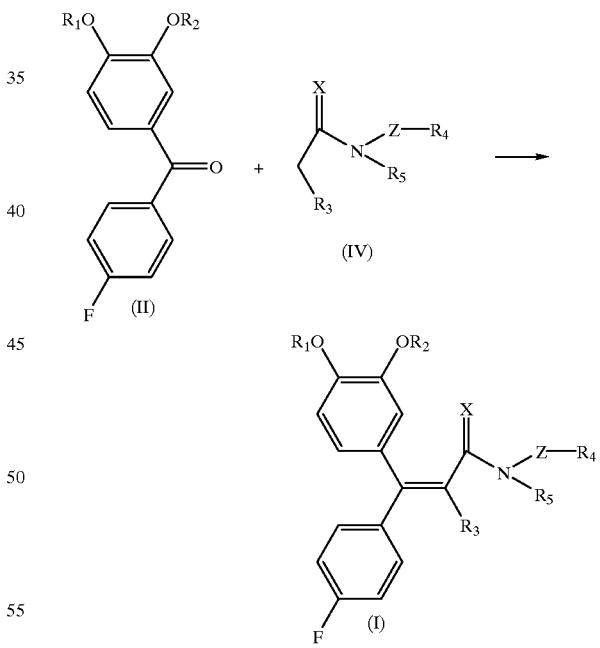

The method 1 and method 2, reactions are carried out in an inert solvent (benzene, toluene, xylene, ethyl ether, tetrahydrofuran, dichloromethane, ethanol) in the presence of a strong alkali (sodium hydroxide, potassium hydroxide, sodium hydride, potassium tert-butylate, sodium tert-butyrate, sodium methylate, sodium ethylate) as a temperature between 0° C. and the boiling point of the solvent 0.5–24 hours.

Method 3: In method 3 a substituted cinnamic acid (V) is reacted with an substituted amine following in situ activation as described in U.S. Pat. No. 4,753,934. The preparation of substituted cinnamic acids is described in U.S. Pat. No. 4,910,200.

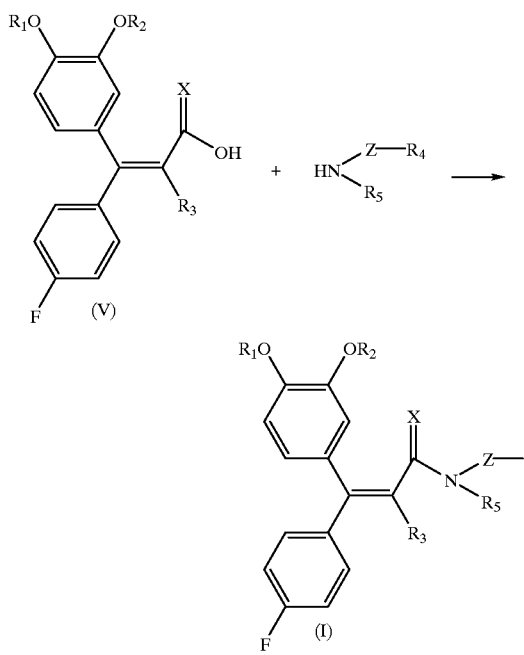

The intermediate (V) is reacted in situ, in an inert solvent such as benzene, methyl benzene, dimethyl benzene, ethyl ether, tetrahydrofuran, dimethylformamide, dichlormethane in the presence of a chlorinating agent such as chlorosulfoxide, phosphorus oxytrichloride, phosphorus trichloride, or phosgene, at a temperature, from 0° C. to the boiling point of the solvent, for 0.5–24 hours, with the secondary amine shown in Method 3.

Method 4: Reaction formula is as follows.

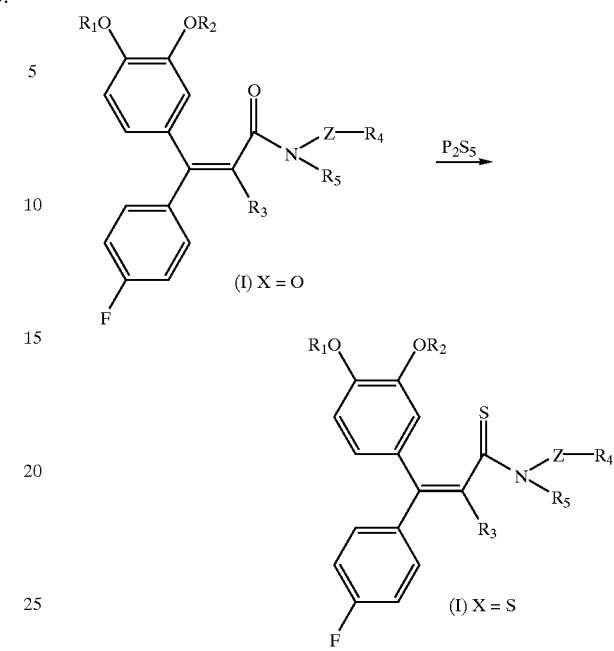

The compound (I) (X=O) is dissolved in an inert solvent (dichloromethane, chloroform, dichloroethane, tetrahydrofuran, benzene, methyl benzene, dimethyl benzene, chlorobenzene, dichlorobenzene, ethyl ether, or acetonitrile), and then it is reacted with phosphorus pentasulfide in the presence of an alkali (triethylamine, sodium hydroxide, potassium hydroxide, sodium bicarbonate, potassium bicarbonate) at a temperature, from −25° C. to the boiling point of the solvent, for 0.5–24 hours, to obtain the title compound (I).

Typical compounds encompassed by the present invention of Formula (I) include those compounds presented in Tables 1 to 5.

TABLE 1

| Ex. No. | $R_1$ | $R_2$ | $R_3$ | X | Z | $R_4$ | $R_5$ |
|---|---|---|---|---|---|---|---|
| 1.01 | $CH_3$ | $CH_3$ | H | O | — | $CH_3$ | $CH_3$ |
| 1.02 | $CH_3$ | $CH_3$ | CN | O | — | $CH_3$ | $CH_3$ |
| 1.03 | $CH_3$ | $CH_3$ | H | O | — | $CH_3$ | $C_2H_5$ |
| 1.04 | $CH_3$ | $CH_3$ | H | O | — | $CH_3$ | $n\text{-}C_3H_7$ |
| 1.05 | $CH_3$ | $CH_3$ | H | O | — | $CH_3$ | $i\text{-}C_3H_7$ |
| 1.06 | $CH_3$ | $CH_3$ | H | O | — | $CH_3$ | $n\text{-}C_4H_9$ |
| 1.07 | $CH_3$ | $CH_3$ | H | O | — | $CH_3$ | $i\text{-}C_4H_9$ |
| 1.08 | $CH_3$ | $CH_3$ | H | O | — | $CH_3$ | $n\text{-}C_5H_{11}$ |

TABLE 1-continued $$\text{(I)}$$

Structure: 4-fluorophenyl and 3,4-di(OR)phenyl groups attached to a C=C, with C(=X)-N(Z-R$_4$)(R$_5$) substituent; R$_3$ on the alkene carbon.

| Ex. No. | R$_1$ | R$_2$ | R$_3$ | X | Z | R$_4$ | R$_5$ |
|---|---|---|---|---|---|---|---|
| 1.09 | CH$_3$ | CH$_3$ | H | O | — | C$_2$H$_5$ | C$_2$H$_5$ |
| 1.10 | CH$_3$ | CH$_3$ | H | O | — | C$_2$H$_5$ | n-C$_3$H$_7$ |
| 1.11 | CH$_3$ | CH$_3$ | H | O | — | C$_2$H$_5$ | i-C$_3$H$_7$ |
| 1.12 | CH$_3$ | CH$_3$ | H | O | — | C$_2$H$_5$ | n-C$_4$H$_9$ |
| 1.13 | CH$_3$ | CH$_3$ | H | O | — | C$_2$H$_5$ | i-C$_4$H$_9$ |
| 1.14 | CH$_3$ | CH$_3$ | H | O | — | C$_2$H$_5$ | n-C$_5$H$_{11}$ |
| 1.15 | CH$_3$ | CH$_3$ | H | O | — | n-C$_3$H$_7$ | n-C$_3$H$_7$ |
| 1.16 | CH$_3$ | CH$_3$ | H | O | — | n-C$_3$H$_7$ | i-C$_3$H$_7$ |
| 1.17 | CH$_3$ | CH$_3$ | H | O | — | n-C$_3$H$_7$ | n-C$_4$H$_9$ |
| 1.18 | CH$_3$ | CH$_3$ | H | O | — | n-C$_3$H$_7$ | i-C$_4$H$_9$ |
| 1.19 | CH$_3$ | CH$_3$ | H | O | — | n-C$_3$H$_7$ | n-C$_5$H$_{11}$ |
| 1.20 | CH$_3$ | CH$_3$ | H | O | — | i-C$_3$H$_7$ | i-C$_3$H$_7$ |
| 1.21 | CH$_3$ | CH$_3$ | H | O | — | i-C$_3$H$_7$ | n-C$_4$H$_9$ |
| 1.22 | CH$_3$ | CH$_3$ | H | O | — | i-C$_3$H$_7$ | i-C$_4$H$_9$ |
| 1.23 | CH$_3$ | CH$_3$ | H | O | — | i-C$_3$H$_7$ | n-C$_5$H$_{11}$ |
| 1.24 | CH$_3$ | CH$_3$ | H | O | — | n-C$_4$H$_9$ | n-C$_4$H$_9$ |
| 1.25 | CH$_3$ | CH$_3$ | H | O | — | n-C$_4$H$_9$ | i-C$_4$H$_9$ |
| 1.26 | CH$_3$ | CH$_3$ | H | O | — | n-C$_4$H$_9$ | n-C$_5$H$_{11}$ |
| 1.27 | CH$_3$ | CH$_3$ | H | O | — | CH$_3$ | cyclopropyl |
| 1.28 | CH$_3$ | CH$_3$ | H | O | — | CH$_3$ | cyclobutyl |
| 1.29 | CH$_3$ | CH$_3$ | H | O | — | CH$_3$ | cyclopropyl |
| 1.30 | CH$_3$ | CH$_3$ | H | O | — | n-C$_3$H$_7$ | cyclopropyl |
| 1.31 | CH$_3$ | CH$_3$ | H | O | — | CH$_3$ | cyclopropyl |
| 1.32 | CH$_3$ | CH$_3$ | H | O | — | CH$_3$ | cyclopropyl |
| 1.33 | CH$_3$ | CH$_3$ | H | O | — | CH$_3$ | cyclopropyl |
| 1.34 | CH$_3$ | CH$_3$ | H | O | — | CH$_3$ | CH$_2$—CCH |
| 1.35 | CH$_3$ | CH$_3$ | H | O | — | CH$_3$ | CH$_2$—CH=CH$_2$ |
| 1.36 | CH$_3$ | CH$_3$ | H | O | — | CH$_3$ | CH$_2$—CC—CH$_3$ |
| 1.37 | CH$_3$ | CH$_3$ | H | O | — | CH$_3$ | CH$_2$—O—CH$_3$ |
| 1.38 | CH$_3$ | CH$_3$ | H | O | — | CH$_3$ | CH$_2$CH$_2$—O—CH$_3$ |
| 1.39 | CH$_3$ | CH$_3$ | H | O | — | CH$_3$ | CH$_2$—O—CH$_2$CH$_3$ |
| 1.40 | CH$_3$ | CH$_3$ | H | O | — | CH$_3$ | CH$_2$CH$_2$—O—CH$_2$CH$_3$ |
| 1.41 | CH$_3$ | CH$_3$ | H | O | — | CH$_3$ | CH$_2$Ph |
| 1.42 | CH$_3$ | CH$_3$ | H | O | — | CH$_3$ | CH$_2$Ph-4-Cl |
| 1.43 | CH$_3$ | CH$_3$ | H | O | — | CH$_3$ | CH$_2$Ph-4-F |
| 1.44 | CH$_3$ | CH$_3$ | H | O | — | CH$_3$ | CH$_2$Ph-3,4-Cl$_2$ |
| 1.45 | CH$_3$ | CH$_3$ | H | O | — | CH$_3$ | CH$_2$Ph-4-OCH$_3$ |
| 1.46 | CH$_3$ | CH$_3$ | H | O | — | CH$_3$ | CH$_2$Ph-4-CH$_3$ |
| 1.47 | CH$_3$ | CH$_3$ | H | O | — | CH$_3$ | (CH$_2$)$_3$Ph |
| 1.48 | CH$_3$ | CH$_3$ | H | O | — | CH$_3$ | CH$_2$CF$_3$ |
| 1.49 | CH$_3$ | CH$_3$ | H | O | — | CH$_3$ | CH$_2$—CCH |
| 1.50 | CH$_3$ | CH$_3$ | H | O | — | CH$_3$ | CH$_2$—CH=CH$_2$ |
| 1.51 | CH$_3$ | CH$_3$ | H | O | — | C$_2$H$_5$ | CH$_2$Ph |
| 1.52 | CH$_3$ | CH$_3$ | H | O | — | C$_2$H$_5$ | CH$_2$—CC—CH$_3$ |
| 1.52 | CH$_3$ | CH$_3$ | H | O | — | C$_2$H$_5$ | CH$_2$—O—CH$_3$ |
| 1.54 | CH$_3$ | CH$_3$ | H | O | — | C$_2$H$_5$ | CH$_2$CH$_2$—O—CH$_3$ |
| 1.55 | CH$_3$ | CH$_3$ | H | O | — | C$_2$H$_5$ | CH$_2$—O—CH$_2$CH$_3$ |
| 1.56 | CH$_3$ | CH$_3$ | H | O | — | C$_2$H$_5$ | CH$_2$CH$_2$—O—CH$_2$CH$_3$ |
| 1.57 | CH$_3$ | CH$_3$ | H | O | — | n-C$_3$H$_7$ | CH$_2$—CC—H |
| 1.58 | CH$_3$ | CH$_3$ | H | O | — | n-C$_3$H$_7$ | CH$_2$—CH=CH$_2$ |
| 1.59 | CH$_3$ | CH$_3$ | H | O | — | n-C$_3$H$_7$ | CH$_2$—CC—CH$_3$ |
| 1.60 | CH$_3$ | CH$_3$ | H | O | — | n-C$_3$H$_7$ | CH$_2$Ph |
| 1.61 | CH$_3$ | CH$_3$ | H | O | O | CH$_3$ | CH$_3$ |
| 1.62 | CH$_3$ | CH$_3$ | H | O | O | CH$_3$ | C$_2$H$_5$ |
| 1.63 | CH$_3$ | CH$_3$ | H | O | O | CH$_3$ | n-C$_3$H$_7$ |
| 1.64 | CH$_3$ | CH$_3$ | H | O | O | CH$_3$ | i-C$_3$H$_7$ |
| 1.65 | CH$_3$ | CH$_3$ | H | O | O | CH$_3$ | n-C$_4$H$_9$ |
| 1.66 | CH$_3$ | CH$_3$ | H | O | O | CH$_3$ | i-C$_4$H$_9$ |
| 1.67 | CH$_3$ | CH$_3$ | H | O | O | CH$_3$ | CH$_2$—O—CH$_3$ |
| 1.68 | CH$_3$ | CH$_3$ | H | O | O | CH$_3$ | CH$_2$CH$_2$—O—CH$_3$ |

TABLE 1-continued $$\text{(I)}$$

Structure: 4-fluorophenyl and 3,4-di(OR) phenyl substituted acrylamide with R₁O, OR₂ on one ring, X=double bond to N-Z-R₄ with R₅ on N, and R₃ on alpha carbon.

| Ex. No. | R₁ | R₂ | R₃ | X | Z | R₄ | R₅ |
|---|---|---|---|---|---|---|---|
| 1.69 | CH₃ | CH₃ | H | O | O | CH₃ | CH₂—O—CH₂CH₃ |
| 1.70 | CH₃ | CH₃ | H | O | O | CH₃ | CH₂CH₂—O—CH₂CH₃ |
| 1.71 | CH₃ | CH₃ | H | O | O | CH₃ | CH₂—CCH |
| 1.72 | CH₃ | CH₃ | H | O | O | CH₃ | CH₂—CH=CH₂ |
| 1.73 | CH₃ | CH₃ | H | O | O | CH₃ | CH₂—CC—CH₃ |
| 1.74 | CH₃ | CH₃ | H | O | O | CH₃ | CH₂Ph |
| 1.75 | CH₃ | CH₃ | H | O | O | CH₃ | CH₂Ph-4-Cl |
| 1.76 | CH₃ | CH₃ | H | O | O | CH₃ | CH₂Ph-4-F |
| 1.77 | CH₃ | CH₃ | H | O | O | CH₃ | CH₂Ph-3,4-Cl₂ |
| 1.78 | CH₃ | CH₃ | H | O | O | CH₃ | CH₂Ph-4-OCH₃ |
| 1.79 | CH₃ | CH₃ | H | O | O | CH₃ | CH₂Ph-4-CH₃ |
| 1.80 | CH₃ | CH₃ | H | O | O | CH₃ | (CH₂)₃Ph |
| 1.81 | CH₃ | CH₃ | H | O | O | CH₃ | CH₂Ph-3,4-Cl₂ |
| 1.82 | CH₃ | CH₃ | H | O | O | C₂H₅ | CH₃ |
| 1.83 | CH₃ | CH₃ | H | O | O | C₂H₅ | C₂H₅ |
| 1.84 | CH₃ | CH₃ | H | O | O | C₂H₅ | n-C₃H₇ |
| 1.85 | CH₃ | CH₃ | H | O | O | C₂H₅ | i-C₃H₇ |
| 1.86 | CH₃ | CH₃ | H | O | O | C₂H₅ | n-C₄H₉ |
| 1.87 | CH₃ | CH₃ | H | O | O | C₂H₅ | CH₂—CCH |
| 1.88 | CH₃ | CH₃ | H | O | O | C₂H₅ | CH₂—CH=CH₂ |
| 1.89 | CH₃ | CH₃ | H | O | O | C₂H₅ | CH₂—CC—CH₃ |
| 1.90 | CH₃ | CH₃ | H | O | O | C₂H₅ | CH₂—O—CH₃ |
| 1.91 | CH₃ | CH₃ | H | O | O | C₂H₅ | CH₂CH₂—O—CH₃ |
| 1.92 | CH₃ | CH₃ | H | O | O | C₂H₅ | CH₂—O—CH₂CH₃ |
| 1.93 | CH₃ | CH₃ | H | O | O | C₂H₅ | CH₂CH₂—O—CH₂CH₃ |
| 1.94 | CH₃ | CH₃ | H | O | O | C₂H₅ | CH₂—O—CH₃ |
| 1.95 | CH₃ | CH₃ | H | O | O | C₂H₅ | CH₂CH₂—O—CH₃ |
| 1.96 | CH₃ | CH₃ | H | O | O | C₂H₅ | CH₂—O—CH₂CH₃ |
| 1.97 | CH₃ | CH₃ | H | O | O | C₂H₅ | CH₂CH₂—O—CH₂CH₃ |
| 1.98 | CH₃ | CH₃ | H | O | O | C₂H₅ | CH₂Ph |
| 1.99 | CH₃ | CH₃ | H | O | O | C₂H₅ | CH₂Ph-4-Cl |
| 1.101 | CH₃ | CH₃ | H | O | O | C₂H₅ | CH₂Ph-4-F |
| 1.102 | CH₃ | CH₃ | H | O | O | C₂H₅ | CH₂Ph-3,4-Cl₂ |
| 1.103 | CH₃ | CH₃ | H | O | O | C₂H₅ | CH₂Ph-4-OCH₃ |
| 1.104 | CH₃ | CH₃ | H | O | O | C₂H₅ | CH₂Ph-4-CH₃ |
| 1.105 | CH₃ | CH₃ | H | O | O | C₂H₅ | (CH₂)₃Ph |
| 1.106 | CH₃ | CH₃ | H | O | O | CH₂—O—CH₃ | CH₂—CC—CH₃ |
| 1.107 | CH₃ | CH₃ | H | O | O | CH₂—O—CH₃ | CH₂Ph |
| 1.108 | CH₃ | CH₃ | H | O | O | CH₂—O—CH₃ | CH₂—O—CH₃ |
| 1.109 | CH₃ | CH₃ | H | O | O | CH₂—CH=CH₂ | CH₃ |
| 1.110 | CH₃ | CH₃ | H | O | O | CH₂—CH=CH₂ | CH₂—CH=CH₂ |
| 1.111 | CH₃ | CH₃ | H | O | O | CH₂—CH=CH₂ | C₂H₅ |
| 1.112 | CH₃ | CH₃ | H | O | O | CH₂—CH=CH₂ | n-C₃H₇ |
| 1.113 | CH₃ | CH₃ | H | O | O | CH₂—CH=CH₂ | CH₂Ph |
| 1.114 | CH₃ | CH₃ | H | O | O | CH₂—CH=CH₂ | CH₂Ph-4-Cl |
| 1.115 | CH₃ | CH₃ | H | O | O | CH₂—CH=CH₂ | CH₂Ph-4-F |
| 1.116 | CH₃ | CH₃ | H | O | O | CH₂—CCH | CH₃ |
| 1.117 | CH₃ | CH₃ | H | O | O | CH₂—CCH | C₂H₅ |
| 1.119 | CH₃ | CH₃ | H | O | O | CH₂—CCH | CH₂—CCH |
| 1.120 | CH₃ | CH₃ | H | O | O | CH₂—CCH | n-C₃H₇ |
| 1.121 | CH₃ | CH₃ | H | O | O | CH₂—CCH | CH₂—O—CH₃ |
| 1.122 | CH₃ | CH₃ | H | O | O | CH₂—CCH | CH₂CH₂—O—CH₃ |
| 1.123 | CH₃ | CH₃ | H | O | O | CH₂—CCH | CH₂Ph-4-Cl |
| 1.124 | CH₃ | CH₃ | H | O | O | CH₂—CCH | CH₂Ph-4-F |
| 1.125 | CH₃ | CH₃ | H | O | O | CH₂Ph | CH₃ |
| 1.126 | CH₃ | CH₃ | H | O | O | CH₂Ph | C₂H₅ |
| 1.127 | CH₃ | CH₃ | H | O | O | CH₂Ph | n-C₃H₇ |
| 1.128 | CH₃ | CH₃ | H | O | O | CH₂Ph | CH₂CF₃ |
| 1.129 | CH₃ | CH₃ | H | O | — | CH₃ | CH₂—A |
| 1.130 | CH₃ | CH₃ | H | O | — | C₂H₅ | CH₂—A |

TABLE 1-continued

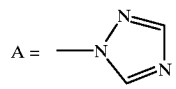

(I)

| Ex. No. | R₁ | R₂ | R₃ | X | Z | R₄ | R₅ |
|---|---|---|---|---|---|---|---|
| 1.131 | CH₃ | CH₃ | H | O | — | n-C₃H₇ | CH₂—A |
| 1.132 | CH₃ | CH₃ | H | O | — | i-C₃H₇ | CH₂—A |
| 1.33 | CH₃ | CH₃ | H | O | — | CH₃ | CH₂—B |
| 1.134 | CH₃ | CH₃ | H | O | — | C₂H₅ | CH₂—B |
| 1.135 | CH₃ | CH₃ | H | O | — | n-C₃H₇ | CH₂—B |
| 1.136 | CH₃ | CH₃ | H | O | — | i-C₃H₇ | CH₂—B |
| 1.137 | CH₃ | CH₃ | H | O | O | CH₃ | CH₂—A |
| 1.138 | CH₃ | CH₃ | H | O | O | CH₃ | CH₂—B |
| 1.139 | CH₃ | CH₃ | H | O | O | CH₃ | CH₂—D |
| 1.140 | CH₃ | CH₃ | H | O | O | CH₃ | CH₂—E |
| 1.141 | CH₃ | C₂H₅ | H | O | O | CH₃ | CH₃ |
| 1.142 | C₂H₅ | CH₃ | H | O | O | CH₃ | CH₃ |

A = 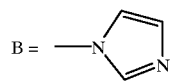

B = 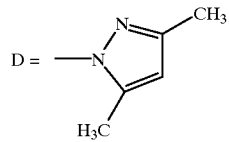

D = 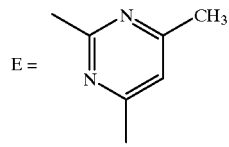

E =

TABLE 2

| Ex. No. | R₄ | R₅ | R₆ | R₇ | Z |
|---|---|---|---|---|---|
| 2.01 | CH₃ | CH₃ | H | H | — |
| 2.02 | C₂H₅ | C₂H₅ | H | H | — |
| 2.03 | n-C₃H₇ | n-C₃H₇ | H | H | — |
| 2.04 | i-C₃H₇ | i-C₃H₇ | H | H | — |
| 2.05 | CH₃ | C₂H₅ | H | H | — |
| 2.06 | CH₃ | i-C₃H₇ | H | H | — |
| 2.07 | CH₃ | n-C₄H₉ | H | H | — |
| 2.08 | CH₃ | i-C₃H₇ | H | H | — |
| 2.09 | CH₃ | CH₃ | H | H | O |
| 2.10 | C₂H₅ | C₂H₅ | H | H | O |
| 2.11 | n-C₃H₇ | n-C₃H₇ | H | H | O |
| 2.12 | i-C₃H₇ | CH₂—CCH | H | H | O |
| 2.13 | CH₃ | CH₂—CH=CH₃ | H | H | O |
| 2.14 | CH₃ | CH₂Ph | H | H | O |
| 2.15 | C₂H₅ | CH₃ | H | H | O |
| 2.16 | C₂H₅ | n-C₃H₇ | H | H | O |
| 2.17 | C₂H₅ | i-C₃H₇ | H | H | O |
| 2.18 | CH₃ | CH₂—CCH | H | H | O |

| | | | | | |
|---|---|---|---|---|---|
| 2.19 | $C_2H_5$ | $CH_2Ph$-4-F | H | H | O |
| 2.20 | $CH_3$ | $CH_3$ | F | F | O |
| 2.21 | $C_2H_5$ | $C_2H_5$ | F | F | O |
| 2.22 | $CH_3$ | $C_2H_5$ | F | F | O |
| 2.23 | $n$-$C_3H_7$ | $n$-$C_3H_7$ | F | F | O |
| 2.24 | $i$-$C_3H_7$ | $i$-$C_3H_7$ | F | F | O |
| 2.25 | $CH_3$ | $CH_2$—CCH | F | F | O |
| 2.26 | $CH_3$ | $CH_2Ph$ | F | F | O |
| 2.27 | $C_2H_5$ | $CH_3$ | F | F | O |
| 2.28 | $C_2H_5$ | $n$-$C_3H_7$ | F | F | O |
| 2.25 | $CH_3$ | $CH_3$ | F | F | — |
| 2.26 | $C_2H_5$ | $C_2H_5$ | F | F | — |
| 2.27 | $CH_3$ | $C_2H_5$ | F | F | — |
| 2.28 | $CH_3$ | $n$-$C_3H_7$ | F | F | — |
| 2.29 | $CH_3$ | $CH_2$—CCH | F | F | — |
| 2.30 | $C_2H_5$ | $CH_2$—CCH | F | F | — |
| 2.31 | $CH_3$ | $CH_2Ph$ | F | F | — |
| 2.32 | $n$-$C_3H_7$ | $n$-$C_3H_7$ | F | F | — |
| 2.33 | $CH_3$ | $CH_2$—A | F | F | — |
| 2.34 | $C_2H_5$ | $CH_2$—A | F | F | — | where $R_3$ = H and X = O
where A is 1H-1,2,4-triazole

TABLE 3

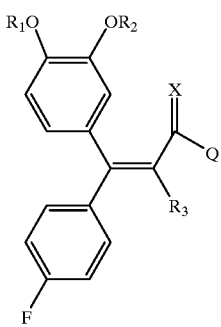

| Ex. No. | $R_1$ | $R_2$ | $R_3$ | Q |
|---|---|---|---|---|
| 3.01 | $CH_3$ | $CH_3$ | H | Q1 |
| 3.02 | $CH_3$ | $CH_3$ | H | Q2 |
| 3.03 | $CH_3$ | $CH_3$ | H | Q3 |
| 3.04 | $CH_3$ | $CH_3$ | H | Q4 |
| 3.05 | $CH_3$ | $CH_3$ | H | Q5 |
| 3.06 | $CH_3$ | $CH_3$ | H | Q6 |
| 3.07 | $CH_3$ | $CH_3$ | H | Q7 |
| 3.08 | $CH_3$ | $C_2H_5$ | H | Q1 |
| 3.09 | $C_2H_5$ | $CH_3$ | H | Q2 |
| 3.10 | $C_2H_5$ | $CH_3$ | H | Q3 |
| 3.11 | $C_2H_5$ | $CH_3$ | H | Q4 |
| 3.12 | $C_2H_5$ | $CH_3$ | H | Q5 |
| 3.13 | $C_2H_5$ | $CH_3$ | H | Q6 |
| 3.14 | $C_2H_5$ | $CH_3$ | H | Q7 |
| 3.15 | $CH_3$ | $C_2H_5$ | H | Q2 |
| 3.16 | $CH_3$ | $C_2H_5$ | H | Q3 |
| 3.17 | $CH_3$ | $C_2H_5$ | H | Q4 |
| 3.18 | $CH_3$ | $C_2H_5$ | H | Q5 |
| 3.19 | $CH_3$ | $C_2H_5$ | H | Q6 |
| 3.20 | $CH_3$ | $C_2H_5$ | H | Q7 |
| 3.21 | $CH_3$ | $CH_3$ | CN | Q1 |
| 3.22 | $CH_3$ | $CH_3$ | CN | Q2 |
| 3.23 | $CH_3$ | $CH_3$ | CN | Q3 |
| 3.24 | $CH_3$ | $CH_3$ | CN | Q4 |
| 3.25 | $CH_3$ | $CH_3$ | CN | Q5 |
| 3.26 | $CH_3$ | $CH_3$ | CN | Q6 |
| 3.27 | $CH_3$ | $CH_3$ | CN | Q7 |
| 3.28 | $CH_3$ | $C_2H_5$ | CN | Q1 |
| 3.29 | $C_2H_5$ | $CH_3$ | CN | Q2 |
| 3.30 | $C_2H_5$ | $CH_3$ | CN | Q3 |
| 3.31 | $C_2H_5$ | $CH_3$ | CN | Q4 |
| 3.32 | $C_2H_5$ | $CH_3$ | CN | Q5 |
| 3.33 | $C_2H_5$ | $CH_3$ | CN | Q6 |
| 3.34 | $C_2H_5$ | $CH_3$ | CN | Q7 |
| 3.35 | $CH_3$ | $C_2H_5$ | CN | Q2 |
| 3.36 | $CH_3$ | $C_2H_5$ | CN | Q3 |

TABLE 3-continued

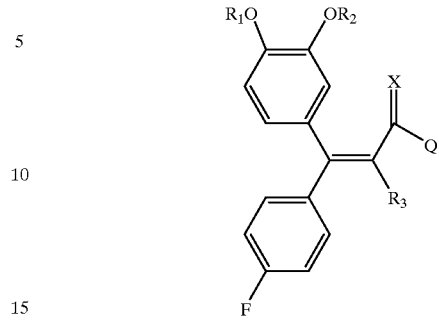

| Ex. No. | $R_1$ | $R_2$ | $R_3$ | Q |
|---|---|---|---|---|
| 3.37 | $CH_3$ | $C_2H_5$ | CN | Q4 |
| 3.38 | $CH_3$ | $C_2H_5$ | CN | Q5 |
| 3.39 | $CH_3$ | $C_2H_5$ | CN | Q6 |
| 3.40 | $CH_3$ | $C_2H_5$ | CN | Q7 | where X = O

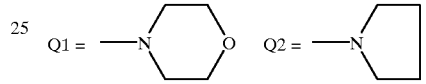
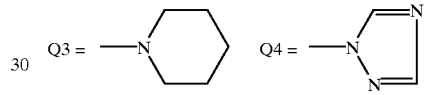
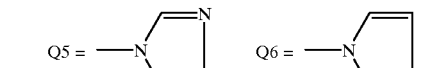

TABLE 4

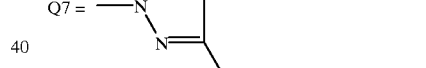

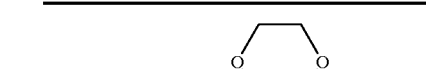

$R_3$ = H, CN
X = O

TABLE 5

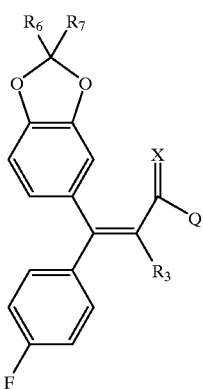

| Ex. No. | R3 | R6 | R7 | Z |
|---|---|---|---|---|
| 5.01 | H | H | H | Q1 |
| 5.02 | H | H | H | Q2 |
| 5.03 | H | H | H | Q3 |
| 5.04 | H | H | H | Q4 |
| 5.05 | H | H | H | Q5 |
| 5.06 | H | H | H | Q6 |
| 5.07 | H | H | H | Q7 |
| 5.08 | CN | H | H | Q1 |
| 5.09 | CN | H | H | Q2 |
| 5.10 | CN | H | H | Q3 |
| 5.11 | CN | H | H | Q4 |
| 5.12 | CN | H | H | Q5 |
| 5.13 | CN | H | H | Q6 |
| 5.14 | CN | H | H | Q7 |

Where Q1–Q7 are understood to be the same as defined in Table 3. As used in Tables 1–5 CC is understood to represent a triple bond between the carbon atoms. Ph as used in Tables 1–5 is aryl. Compounds of Formula (I) of this invention can be prepared as described in Example 6.

EXAMPLE 6

[Preparation of 4-(3-(4-fluorophenyl)-3-(3,4-dimethoxyphenyl)acryloyl)morpholine (Compound I), Example 3.01 of Table 3]

4-Fluoro-3',4'-dimethoxy diphenyl ketone 26 g (0.1 mol) was added in a mixed solution of sodium tert-butylate (0.15–0.35 mol) containing methylbenzene 380 ml and tert-butanol 30 ml. While being heated and agitated to reflux, methyl benzene solution 50 ml that contained acetyl morpholine (0.15–0.35 mol) was added over a period of 5–8 hours. It was refluxed to react, meantime distilling off the tert-butanol, for 6–12 hours (reaction was traced by TLC). After completing the reaction, reaction mixture was cooled, the methyl benzene layer was washed with water, dehydrated over anhydrous magnesium sulfate to remove the solvent, and then it was let stand to form crystals. It was recrystallized from methanol, to yield a product 31.5–34.0 g (yield=88–95%).

Melting point=120–128° C. (Z/E mixture ratio=55/45).
IR (KBr disc): 1625 $cm^{-1}$ (—CO—)
1H NMR (DMCO, internal standard=tetramethylsilane, 90 MHz) d: =CH—CO—, cis-: 6.21 ppm, trans: 6.35 ppm cis- and trans-isomers can be separated by further processing.

Example 6 is to be illustrative of the present invention and other compounds of this invention can be prepared by using similar methods described herein.

The compounds of the present invention are useful as agricultural fungicides and, as such, can be applied to various loci such as the seed, the soil or the foliage. The compounds can be applied as fungicidal sprays by methods commonly employed, such as conventional high-gallonage hydraulic sprays, low-gallonage sprays, air-blast spray, aerial sprays and dust. The dilution and rate of application will depend upon the type of equipment employed, the method of application, plants to be treated and diseases to be controlled. Generally, the compounds of this invention will be applied in amount of from about 0.005 kilogram to about 50 kilograms per hectare and preferably from about 0.025 to about 25 kilograms per hectare of the active ingredient.

As a seed protectant, the amount of compound coated on the seed is usually at a dosage rate of from about 0.05 to about 20, preferably from about 0.05 to about 4, and more preferably from about 0.1 to about 1 grams per hundred kilograms of seed. As a soil fungicide the compounds can be incorporated in the soil or applied to the surface usually at a rate of from about 0.02 to about 20, preferably from about 0.05 to about 10, and more preferably from about 0.1 to about 5 kilograms per hectare. As a foliar fungicide, the toxicant is usually applied to growing plants at a rate of from about 0.01 to about 10, preferably from about 0.02 to 5, and more preferably from about 0.25 to about 1 kilograms per hectare.

Inasmuch as the compounds of the invention, display fungicidal activity, these compounds can be combined with other known fungicides to provide broad spectrum activity. Suitable fungicides include, but are not limited to, those compounds listed in U.S. Pat. No. 5,252,594 (see in particular columns 14 and 15).

Since the compounds possess broad spectrum fungicidal activity, they can be employed in the storage of cereal grain. These complexes can also be employed as fungicides in cereals including wheat, barley and rye, in rice, peanuts, beans and grapes, on turf, in fruit, nut and vegetable orchards, and for golf course applications.

Examples of diseases against which the compounds of the invention are useful include helminthosporium of corn and barley, wheat and barley powdery mildew, wheat leaf and stem rusts, tomato early blight, tomato late blight, peanut early leaf spot, grape powdery mildew, grape black rot, apple scab, apple powdery mildew, cucumber powdery mildew, brown rot of fruits, botrytis, bean powdery mildew, cucumber anthracnose, wheat septoria nodorum, rice sheath blight and rice blast.

In the practice of the method of the invention, the active compound may be applied to the solid or foliage where it is absorbed by the plant, translocated to other plant parts and ultimately ingested by the pest or insects by means of ingestion of the plant part(s). This means of application is referred to as "systemic" application. Alternatively, the active compound may be applied to the soil and contacted therein with the insects and other pests to be controlled. This means of application is referred to as "soil" application. In another alternative, the active compound may be foliarly applied to the plants to be freed from insects and other pests which feed on the foliage.

The compounds of the present invention can be used in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations", (1973) edited by Wade Van Valkenburg. In these compositions and formulations, the active substance is mixed with conventional inert agronomically acceptable (i.e., plant compatible and/or pesticidally inert) pesticide diluents or extenders such as solid carrier material or liquid carrier material, of the type usable in conventional pesticide compositions or formulations. By "agronomically acceptable carrier is meant any substance which can be used to dissolve, disperse of diffuse the active ingredient in the composition without impairing the active ingredients effectiveness and which by itself has no significant detrimental effect on the soil, equipment, desirable plants, or agronomic environment. If desired, adjuvants such as surfactants, stabilizers, antifoam agents and antidrift agents may also be combined.

Examples of compositions and formulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles. Wettable powders, pastes, flowables and emulsifiable concentrates are concentrated preparations which are diluted with water before or during use. In such formulations, the compounds are extended with a liquid or solid carrier and, when desired, suitable surfactants are incorporated. Baits are preparations generally comprising a food or other substance attractive to insects, that includes at least one compound of the instant invention.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art, and a discussion of adjuvants can be found in many references, such as in the John W. McCutcheon, Inc. publication "Detergents and Emulsifiers, Annual."

The active compounds of the present invention may be employed alone or in the form of mixtures with one another and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists.

In the compositions of the invention, the active compound is present in an amount substantially between about 0.0001–99% by weight. For compositions suitable for storage or transportation, the amount of active ingredient is preferably between about 0.5–90% by weight, and more preferably between about 1–75% by weight of the mixture. Compositions suitable for direct application or field application generally contain the active compound in an amount substantially between about 0.0001–95%, preferably between about 0.0005–90% by weight, and more preferably between about 0.001–75% by weight of the mixture. The composition can also be stated as a ratio of the compound to the carrier. In the present invention the weight ratio of these materials (active compound/carrier) can vary from 99:1 to 1:4 and more preferably from 10:1 to 1:3.

In general, the compounds of this invention can be dissolved in certain solvents such as acetone, methanol, ethanol, dimethylformamide, pyridine or dimethyl sulfoxide and such solutions can be diluted with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent to enhance dispersion of the compound in water. The concentration of the active ingredient in emulsifiable concentrates is usually from about 10% to about 90%, and in flowable emulsion concentrates, can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of from about 20% to about 99%, preferably from about 40% to about 75%. A typical wettable powder is made by blending 50 parts of a pyridazinone, 45 parts of a synthetic precipitated hydrated silicon dioxide, such as that sold under the trademark Hi-SilR, and 5 part of sodium lignosulfonate. In another preparation of kaolin type (Barden) clay is used in place of the Hi-Sil in the above wettable powder, and in another such preparation 25% of the Hi-Sil is replaced with a synthetic sodium silicoaluminate sold under the trademark Zeolex® 7.

The compound (I) of this invention can be used alone or can be mixed with one, two or more fungicidal agent(s) or insecticide(s) to form a binary or ternary mixture, for application. Suitable insecticides known in the art include those listed in U.S. Pat. No. 5,075,471, see in particular columns 14 and 15. Specific insecticides that can be mixed and used together with the compound (I) of this invention include Bromopropylate, Tedion, Methyl 1605, 1605, Sumithion, Diazinon, Dursban, Mimic, Aphistar, Methomyl, Tetrachlorovinphos, Methidathion, Cartap, Sevin, NRDC 143, Chlorocyano pyrethrate, Tetramethrin, Heptafluoro pyrethrate, Fluorochlorocyano pyrethrate, Cyanopenta pyrethrate, PH 60-40, Saziron, Pyrazophos, Acar, Imidacloprid, Fipronil, NI-25, Dioxacarb, Neotran, Methamidophos, Tamarin, and Clofentezine.

Suitable fungicidal agents that can be mixed with the title compound (I) of this invention include, but are not limited to, Captan, Phaltan, Zineb, Mancozeb, Thiram, Difoltan, Iprodione, Methyl dichlozoline, Methylethyl dichlorozoline, Hexaconazole, Myclobutanil, Tebuconazole, DPX-3217, diguanidoacetoacetate salt, Diethofencarb, Cyprofuram, allylazole, Flutolanil, Carbendazim, Benomyl, Triazolone, Cyproconazole, Methyl thiophanate, Hydroxyoxazole, Butylphenyl morpholine, Triazolone, Cyproconazole, Methyl thiophanate, Hydroxyoxazole, Butylphenyl morpholine, Propamocarb, Metalaxyl, Furalaxyl, Benalaxyl, Methasulfocarb, Pyrifenox, Fenpropidin, Kresoxim-methyl, Azoxystrobin, Fenbuconazole, Thifluzamide, Mepanipyrim, Dimethomorph, Mycotox, Seedvax, Azaconazole, Chlorothalonil, Diazinon, copper sulfate, Dichlorofluamid, aluminium phosphide, and Hymexazol.

In the prepared mixture, the content of the compound (I) of this invention is 1%–99% and the other active ingredients may make up from 99–1% by weight of the active ingredients. Preferred combinations include 3-(4-fluorophenyl)-3-(3,4-dimethoxyphenyl)acryl morpholine and mancozeb in a weight ratio of 1:10 to 1:1 and —(4-fluorophenyl)-3-(3,4-dimethoxyphenyl)acryl morpholine and fenbuconazole in a weight ratio of 1:10 to 10:1.

Examples of the carriers that can be used include for the powder, wettable powder, and granules are kieselghur, clay, gypsum, talc powder and kaolin. Solvent that can be used in the emulsion are benzene, toluene, xylene, alkyl benzene, chlorinated cyloalkylenes, $C_{1-6}$ aliphatic alcohols, benzyl alcohol, cyclohexanol, acetone, methylethyl ketone, methyl isobutyl ketone, cyclohexanone, dimethyl formamide, dimethylsulfoxide, N-methylpyrrolidone, water and the like.

The compounds of Formula (I) of this invention can be prepared as an emulsion, powder, wettable powder, granule or a colloidal suspension. Cationic, anionic or nonionic surface active agent may be added as an emulsifier, dispersing agent or wetting agent to the preparation. For example, sodium dodecylsulfonate, sodium dodecylbenzene sulfonate, polyethylenoxy aliphatic acid ester, polyethylenoxy aliphatic acid alcohol, polyethylenoxy aliphatic acyl amine, ethoxylated castor oil, sodium (or potassium) ligninsulfonate, carboxymethyl alcohol, polvinyl alcohols, polyvinyl esters can be used.

EXAMPLE 7

Compound 1 of this invention 40 weight % kieselghur, 53 weight %, $C_{12-20}$ alcohol/sulfate ester 4 weight %, and sodium dodecylbenzensulfonate 3 weight % were mixed homogeneously, and pulverized, to obtain a wettable powder that contained effective component at 40 weight %.

EXAMPLE 8

Compound 1 of this invention 30 weight %, xylene 33 weight %, dimethylformamide 30 weight % and polyethylenoxyalkyl propyl ether 7 weight % were mixed homogeneously and dissolved, to obtain an emulsion that contained effective component at 30 weight %.

EXAMPLE 9

Compound 1 of this invention 10 weight %, talc powder 89 weight %, and polyethylenoxyalkyl propyl ether 1 weight % were mixed homogeneously, and pulverized, to obtain a powder that contained effective component at 10 weight %.

EXAMPLE 10

Compound 1 of this invention 5 weight %, bentonite 20 weight %, sodium dioctyl thiosuccinate 1 weight %, and sodium phosphate 1 weight % were mixed homogeneously. After pulverizing thoroughly, a proper amount of water was added, and they were blended thoroughly, pelletized and dried, to obtain granules that contained effective component 5 weight %.

EXAMPLE 11

Compound 1 of this invention 10 weight %, sodium ligninsulfonate 4 weight %, sodium dodecylbenzene-sulfonate 1 weight %, xantic acid 0.2 weight %, and water 84.8 weight % were mixed homogeneously, and they were wet-ground to a particle size of 1 mm or smaller, to obtain a colloidal suspension that contained effective component 10 weight %.

EXAMPLE 12

Compound 1 of this invention 8 weight %, zinc maneb 50 weight %, kaolin 30 weight %, sodium dodecylbenzene sulfonate 4 weight %, and sodium ligninsulfonate 8 weight % were mixed and pulverized thoroughly, to obtain a wettable powder that contained the mixture 58 weight %.

EXAMPLE 13

Compound 1 of this invention 10 weight %, azaconazole 30 weight %, kaolin 45 weight %, sodium dodecylbenzenesulfonate 6 weight %, and sodium ligninsulfonate 9 weight % were mixed homogeneously, and then pulverized thoroughly, to obtain a wettable powder that contained the mixture 40 weight %.

Compared to the existing antimicrobial agents, the compound of this invention has very good biological activity, and it can be used to prevent damages caused by spores and mycelial pathogens, and particularly effective against downy mildew, blight, and rot, such as apple root knot rot, citrus rot, pepper rot, pumpkin rot, potato late blight, diseases of fig, tomato brown rot, diseases of onion, rot of yellow melon, tobacco black wilting, downy mildew of yellow melon, downy mildew of grape, and red root rot of strawberry. In Examples 14 to 20, Compound 1 is used as an example to demonstrate the fungicidal efficacy of compounds of Formula (I) of this invention.

EXAMPLE 14

Test for inhibition of spore germination in cucumber downy mildew (*Pseudoperonospora cubensis*). Concentration of the test Compound 1 (content: 9% in emulsion oil) was set at 100, 50 and 25 ppm. Dimethomorph (commercially available product) Concentration was 50% wettable powder) was set a 50 ppm, and a blank was set up also as a control. Fresh fungal layer was taken from the leaves which were infected by downy mildew, and a spore suspension was prepared. This spore suspension was mixed with the solution of the test compound, and each treatment was run 6 times. Treated sample was kept in a constant temperature incubator (25° C.), and result was examined after 24 hours. Eighteen fields were examined for each treatment, and the numbers of germinated spores and ungerminated spores were counted. Thus, % inhibition of the spore germination was calculated, and results are shown in Table 6.

Results of the spore germination test shown in Table 6 demonstrate the following: Compound 1 has a highly effective in inhibiting spore germination, and its inhibitory action is superior to Dimethomorph. % Inhibition of spore germination by the compound 1 at 25, 50 and 100 ppm was 65.2%, 93.5%, and 97.6%, respectively. With Dimethomorph at 50 ppm, % inhibition of spore germination was 42.5%.

TABLE 6

Results of the test for inhibition of spore germination by compound 1

| | Compound tested | | | | |
|---|---|---|---|---|---|
| | Compound 1 | | | Dimethmorph | |
| | 25 ppm | 50 ppm | 100 ppm | 50 ppm | CK |
| Number of spores germinated | 198 | 45 | 17 | 208 | 383 |
| Number of ungerminated spores | 660 | 990 | 1044 | 336 | 194 |
| % Spore germination | 23.1 | 4.3 | 1.6 | 38.2 | 66.4 |
| % Inhibition of spore | 65.2 | 93.5 | 97.6 | 42.5 | |

CK is the untreated check.

EXAMPLE 15

Test (indoor) for protection and therapeutic effects against cucumber downy mildew. Concentration of test Compound 1 (content was 9% in emulsion oil) was set at 250, 200, 150, 100 and 75 ppm. Dimethomorph (American Cyanamid) 150 ppm was used as the control. Healthy seedling of yellow melon was selected for use, and test was run three times. For protection test, treatment was carried out on Sep. 17, 1995, and they were inoculated 24 hours later. For the therapeutic test, inoculation was made on September 18, and then they were treated 24 hours later. Examination was made a week later, and results were recorded in 9 grades, and disease index and protection effect were calculated. Results are shown in Table 7.

TABLE 7

Result of test for protection and therapy with compound 1

| | Concen- | Protection | | Therapeutic | |
|---|---|---|---|---|---|
| Compound | tration (ppm) | Disease index | Protection (%) control | Disease index | (%) control |
| Compound 1 | 250 | 0 | 100 | 0 | 100 |
| | 200 | 0 | 100 | 0.01 | 98.1 |
| | 150 | 0 | 100 | 0 | 100 |
| | 100 | 0 | 100 | 0.08 | 84.6 |
| | 75 | 0.03 | 92.5 | 0.11 | 78.8 |
| Dimethmorph | 150 | 0 | 100 | 0.19 | 63.5 |
| Check (untreated) | — | 0.40 | — | 0.52 | — |

Results of protection and therapy tests demonstrate the following: Protective effect of compound 1 is better than the therapeutic effect. Protective effect was 100% and therapeutic effect was 84.6% when the concentration of compound 1 was 100 ppm. Protective effect was 92.5% and therapeutic effect was 78.8% when the concentration of compound 1 was 75 ppm. It was discovered also that the protective effect of the compound agreed with that of Dimethomorph at a concentration of 150 ppm or lower. However, therapeutic effect of the compound 1 was obviously better than Dimethomorph. Thus, therapeutic effect of Compound 1 at 150 ppm was 100%, whereas that of Dimethomorph was 63.5%. And, when the concentration of compound 1 was 75 ppm, the therapeutic effect was better than Dimethomorph at 150 ppm.

EXAMPLE 16

Comparison (indoor test) of anti-Downy mildew activities of Compound 1 and Dimethomorph. Test was divided into test for therapy and test for protection. Concentration of two chemicals (Compound 1 and Dimethomorph) was set at 150 and 100 ppm, and each treatment was run three times. A blank control was set separately. Samples were selected from seedling of yellow melon in the 2–3 leaf stage. Method of treatment and study was the same as before. Results are shown in Table 8.

TABLE 8

Results of comparison of the activities of compound 1 and Dimethomorph

| | Concen- | Protective effect | | Therapeutic effect | |
|---|---|---|---|---|---|
| Compound | tration (ppm) | Disease index | Protective effect (%) control | Disease index | (%) control |
| Compound 1 | 100 | 0.07 | 93 | 0.37 | 63 |
| | 150 | 0.05 | 95 | 0.26 | 74 |
| Dimethomorph | 100 | 0.39 | 61 | 0.98 | 2 |
| | 150 | 0.21 | 79 | 0.76 | 24 |
| untreated | — | 1.00 | — | 1.00 | — |

Results of the comparison of the activities of Compound 1 and Dimethomorph demonstrate the following. Therapeutic and protective effects of Compound 1 were obviously better than the Dimethomorph. Protective effect of Compound 1 was 93% and therapeutic effect was 63% at 100 ppm. At 150 ppm of Compound 1, therapeutic effect was 74% and protective effect was 95%. At Dimethomorph 100 ppm, protective effect was 61% and therapeutic effect was only 2%. At Dimethomorph 150 ppm, protective effect was 89% and therapeutic effect was 24%.

EXAMPLE 17

Comparison (indoor test) of the activities of Compound 1 and the currently available antimicrobial agent against cucumber downy mildew.

The tests were divided into therapeutic effect and protective effect. Concentration of the Compound 1 was set at 200, 100, 75, 50 and 25 ppm. Concentration of the control was set with metalaxyl (500 ppm), aluminium phosphide (1000 ppm), Chlorothalonil (1000 ppm), Previcur (1000 ppm). Each treatment was run three times, and a blank control was set separately also. Seedling of yellow melon (2nd and 3rd leaf stage) was selected to use as a sample. Methods of treatment and testing were the same as before. Results are shown in Table 9.

TABLE 9

Results of comparison of the activities of compound 1 and the existing antimicrobial agents

| | Concentration (ppm) | Protective effect/ preventive (%) control | Therapeutic effect (%) control |
|---|---|---|---|
| Compound 1 | 25 | 40.0 | 0.0 |
| | 50 | 60.0 | 40.0 |
| | 75 | 75.0 | 60.0 |
| | 100 | 90.0 | 75.0 |
| | 200 | 100.0 | 90.0 |
| metalaxyl | 500 | 60.0 | 40.0 |
| Aluminium phosphide | 1000 | 75.0 | 40.0 |
| Chlorothalonil | 1000 | 90.0 | 75.0 |

TABLE 9-continued

Results of comparison of the activities of compound 1 and the existing antimicrobial agents

|  | Concentration (ppm) | Protective effect/ preventive (%) control | Therapeutic effect (%) control |
|---|---|---|---|
| Previcur | 1000 | 90.0 | 0.0 |
| untreated |  | 0.0 | 0.0 |

As we can see in Table 9, protective effect and therapeutic effect of Compound 1 (1000 ppm) are equivalent to Chlorothalonil (1000 ppm), but it is obviously superior to the preventive effect of metalaxyl, aluminium phosphide, and Previcur.

EXAMPLE 18

Protective action (field test)

Field protection test against cucumber downy mildew was carried out in the farm at a village near Shenyang City.

Concentration of the Compound 1 (20% wettable powder) was set at 200, 400 and 600 ppm. Concentration of Previcur (66.5% hydrate) which was used as the control, was set at 800, 1000 and 1200 ppm. And, a blank control was set separately also. Each treatment was run 4 times. Samples were taken for examination. First treatment was carried out on April 5, infected stands were seen at the center; second treatment on April 17, spread of infection was seen; and third treatment was on April 22. First examination of protective effect was made on April 22. The second examination of protective effect was made on April 29, and the third examination of protective effect was made on May 5. Results are shown in Table 10.

TABLE 10

Result of the protective effect of compound 1 against the cucumber downy mildew in the field

|  |  | April 22 | | April 29 | | May 5 | |
|---|---|---|---|---|---|---|---|
| Chemical | Concentration (ppm) | Disease index | Protective (%) control | Disease | Protective (%) control | Disease | Protective (%) control |
| Compound 1 | 200 | 0 | 100 | 0 | 100 | 0.03 | 97.0 |
|  | 400 | 0 | 100 | 0 | 100 | 0 | 100 |
|  | 600 | 0 | 100 | 0 | 100 | 0 | 100 |
| Previcur* | 800 | 0.08 | 89.2 | 0.21 | 77.2 | 0.59 | 41.0 |
|  | 100 | 0.06 | 91.6 | 0.16 | 82.6 | 0.42 | 58.0 |
|  | 1200 | 0.03 | 95.9 | 0.10 | 89.1 | 0.32 | 68.0 |
| CK |  | — | 0.74 | — | 0.92 | — | 1.00 | — |

*"Previcur": A product of Schering Co. which is also known as "Propamocarb".

As we can see in Table 10, Compound 1 (at 200, 400, and 600 ppm) showed a far better protective effect than Previcur (at 800, 1000, and 1200 ppm). With the extension of the interval of the application of the chemical, difference of the effects between these two chemicals became even more obvious.

EXAMPLE 19

Therapeutic effect (field test).

Field therapeutic test of the compound 1 against cucumber downy mildew was carried out in a farm at a village near Shenyang City.

Concentration of the Compound 1 (20% wettable powder) was set at 100, 200 and 300 ppm. Chlor 1500 ppm was used as the control, and blank control was set separately also. Each treatment was repeated three times. First treatment was made on May 13, second treatment was made on May 20, and third treatment was made on May 27, and protective effect was examined on June 3. Results are shown in Table 11.

As we can see in Table 11, therapeutic effect of the compound 1 at 100 ppm was slightly better than Chlor at 1500 ppm. Compound 1 at 200 and 300 ppm showed as obviously better therapeutic effect, compared to that of Chlor at 1500 ppm.

TABLE 11

Result of therapeutic test of compound 1 against cucumber downy mildew in the field

| Chemical | Concentration (ppm) | Disease index | Protective effect (%) control |
|---|---|---|---|
| Compound 1 | 100 | 0.049 | 88.4 |
|  | 200 | 0.011 | 97.4 |
|  | 300 | 0 | 100 |
| Chlor | 1500 | 0.076 | 81.9 |
| untreated | — | 0.422 | — |

*Chlor is a product of DuPont Co. (a mixture of DPX-3217 and Mancozeb).

EXAMPLE 20

Late blight of tomato (field test).

Field therapeutic test of compound 1 against late blight of tomato was carried out in a farm at a village near Shenyang City.

Concentration of Compound 1 (20% wettable powder) was set at 200, 400 and 600 ppm. Dithane (containing 80% wettable powder) 1300 ppm was used as a positive control and a blank control was also used. Treatment was run three times. First treatment was made on May 21, second treatment was made on May 28, and third treatment was made on June 5. And, protective effect was examined on June 20. Results are shown in Table 12.

TABLE 12

Result of field test of the therapeutic effect of compound 1 against late blight of tomato

| Chemical | Concentration (ppm) | Disease index before treatment | Disease index | Protective (%) control |
|---|---|---|---|---|
| Compound 1 | 200 | 0.74 | 5.56 | 80.9 |
|  | 400 | 0.74 | 2.59 | 91.1 |
|  | 600 | 1.11 | 2.22 | 94.9 |
| Dithane | 1300 | 1.11 | 5.56 | 87.3 |
| untreated | — | 1.11 | 43.7 | — |

*Dithane (mancozeb) is a product of Rohm and Haas Company, U.S.A.

As we can see in Table 12, Compound 1 at 400 ppm and 600 ppm showed a better therapeutic effect against late blight of tomato, than Dithane at 1300 ppm.

We claim:

1. The compound 4-(3-(4-fluorophenyl)-3-(3,4-dimethoxyphenyl)acryloyl)morpholine.

2. A fungicidal composition for controlling phytophathogenic fungi which comprises an agronomically acceptable carrier and the compound of claim 1 wherein the ratio of the carrier to the compound is 99:1 to 1:3.

3. The composition of claim 2 wherein the ratio of the agriculturally acceptable carrier to compound is 20:1 to 1:2.

4. The fungicidal mixture of controlling phytophathogenic fungi which comprises 3-(4-fluorophenyl)-3-(3,4-dimethoxyphenyl)acryl morpholine and mancozeb in a weight ratio of 1:10 to 1:1.

5. A fungicidal mixture for controlling phytophathogenic fungi which comprises 3-(4-fluorophenyl)-3-(3,4-dimethoxyphenyl)acryl morpholine and fenbuconazole in a weight ratio of 1:10 to 10:1.

6. A method for controlling phytophathogenic fungi which comprises applying to the locus where control is desired the compound of claim 1 at a rate of from 0.005 to 50 kilograms per hectare.

7. The method of claim 6 wherein the compound of claim 1 is applied at the rate of from 0.025 to 10 kilograms per hectare.

* * * * *